United States Patent [19]
Meyer

[11] 4,202,215
[45] May 13, 1980

[54] SONIC PULSE-ECHO METHOD AND APPARATUS FOR DETERMINING ATTENUATION COEFFICIENTS

[75] Inventor: Charles R. Meyer, Pittsburgh, Pa.

[73] Assignee: Kurt Orban Company, Inc., Wayne, N.J.

[21] Appl. No.: 954,767

[22] Filed: Oct. 26, 1978

[51] Int. Cl.$^2$ ............................................. G01N 29/00
[52] U.S. Cl. ................................... 73/599; 128/660
[58] Field of Search ................ 73/599, 600, 620, 629; 128/660; 340/1 R, 3 R, 5 MP

[56] References Cited

U.S. PATENT DOCUMENTS

| | | | |
|---|---|---|---|
| 3,861,200 | 1/1975 | Dory | 73/599 |
| 4,057,049 | 11/1977 | Hill | 73/570 |
| 4,058,001 | 11/1977 | Waxman | 73/620 |
| 4,138,999 | 2/1979 | Eckhart et al. | 73/599 |

*Primary Examiner*—Stephen A. Kreitman
*Attorney, Agent, or Firm*—Robert D. Yeager; Andrew J. Cornelius

[57] ABSTRACT

A method and apparatus is provided for determining the attenuation coefficients within a body of material by transmitting sonic pressure pulses into the material, analyzing the spectrum amplitude of the echoes returning from the boundaries within the material, calculating the attenuation coefficients of the material between the boundaries and comparing the measured coefficients to those of normal and abnormal tissue. The wave shape of the transmitted pulses is adjusted so that the pulses generate echoes with uniform spectrum amplitude (white echoes) from each boundary within the material. Given the characteristics of the pulses which generate white echoes from the boundaries of each tissue segment and given the thickness of the material between each pair of boundaries, the attenuation coefficients of the material are calculated. The attenuation coefficients are displayed in any manner desired, including traditional B- and M-mode displays.

44 Claims, 10 Drawing Figures

SONIC PULSE-ECHO METHOD AND APPARATUS FOR DETERMINING ATTENUATION COEFFICIENTS

BACKGROUND OF THE INVENTION

1. Field of the Invention

This invention relates to determining the attenuation coefficients within a body of material using sonic pulse techniques and more particularly to the use of sonic pulses to measure attenuation coefficients of internal tissue segments.

2. Description of the Prior Art

Sonic pulse techniques have been used to probe many varying types of material. For example, ultrasonic pressure waves have been used for over twenty years to probe internal tissues of the body in an attempt to diagnose pathological tissue states without invasive surgery. Low energy diagnostic ultrasound has gained popularity in the fields of neurology, ophthalmology, cardiology, obstectrics and gynecology. Most current methods using ultrasonic waves involve transmitting ultrasonic pulses into tissue segments and examining the characteristics of the returning echoes. In one known technique the amplitude of a returning echo is examined to provide an indication of the characteristics of the structure which causes the echo to be created. U.S. Pat. No. 4,058,001 illustrates an embodiment of this technique.

B- and M-scans, which are video displays, are used to generate darkened spots in the video display; the degree of darkness or "gray-scale" of such spots is related to the voltage amplitude of the echo. A paper authored by Gilbert B. Dewey and Peter N. T. Wells, entitled Ultrasound In Medical Diagnosis and published in Scientific American, Volume 238, May 1978, which paper is incorporated by reference herein provides further background in ultrasonic imaging techniques. Unfortunately, variations in amplitude of the returning echoes are related to many concurrent causes such as tissue structure, transducer center frequency and damping, absorption, singular echo duration, and time gain control and settings of the echo receiver. Therefore, it is always unclear whether the amplitude of a particular echo is due to an abnormality in the tissue segment or to one of the other causes set forth above. Interpretation of amplitude displays to determine structures other than simple tissue boundary locations requires a great deal of skill, sophistication, and standardization of echo receiver processing and time gain control settings. For a more detailed treatment of this type of interpretation see J. C. Birnholz, Visual Pattern Recognition and Clinical Ultrasonography, Second International Symposium on Ultrasonic Tissue Characterization, National Bureau of Standards, Session 7, June 7, 1977.

Currently, many investigators are attempting to determine the internal structure of tissue segments by measuring and displaying the physical properties of the segments including such parameters as attenuation coefficient, scattering coefficient, and boundary impedance difference. It is believed that such properties give a better indication of the structure of a tissue segment than the amplitudes of returning ultrasonic echoes. The leading method for generating and displaying these physical parameters is based on through-transmission tomographic reconstruction of ultrasonic wave propagation properties in which method the ultrasonic generating transducer and receiving transducer are separated by a fixed distance and the object to be examined is placed between them. However, through-transmission ultrasound can be used only for the examination of appendages such as breasts and testicles, and not for analysis of tissues deep within the pelvis and chest, because the amplitude of ultrasonic pulses which have passed through such areas are severely attenuated by bone and lung tissue and consequently are too weak to be analyzed with present instrumentation.

Attenuation of ultrasonic waves within tissue segments has received a great deal of attention over the last thirty years. Attenuation within a homogeneous tissue is described as the decrease in amplitude of the propagating ultrasonic wave due to conversion of acoustic energy to other forms of energy and due to scattering. Attenuation is defined as $\alpha(f,l) = \log_e A_1/A_I$ where: $\alpha(f,l)$ is the attenuation and in general is a function of the propagation distance, $l$, and frequency, $f$; $A_1$ is the amplitude of the propagating ultrasonic wave at a distance, $l$, from the generating transducer; and $A_I$ is the initial amplitude of the ultrasonic wave in the medium at the site of the generating transducer. In cases where $\alpha(f,l)$ are proportional to frequency, that is, $\alpha(f,l) = \alpha_i fl$, within a particular tissue, the proportionality constant, $\alpha_i$, is defined as the attenuation coefficient. In a paper by D. E. Goldman and T. F. Hueter, J. Accoustical Society of America, 28:25, 1965, it is shown that attenuation is nearly proportional to ultrasonic frequency in the 1 to 10 MHz range for most tissues having a high protein content. Also, many investigators have shown a high correlation between attenuation in various types of tissue and the existence of abnormalities within that tissue. For a discussion in this subject, see P. P. Lele, et al., Tissue Characterization By Ultrasonic Frequency-Dependent Attenuation And Scattering, National Bureau of Standards Special Publication 453: 172, 1976; J. G. Miller, et al., Ultrasonic Attenuation In Normal And Ischemic Myocardium, National Bureau of Standards, Session 5, June 1977; M. O'Donnell, J. W. Mimbs, et al., Quantitative Collagen Concentration: A Determinate Of Attenuation In Myocardial Infarction, Proceedings AIUM, Sci. Session 2, Paper No. 1112, 1977; C. Calderon, D. Vilkomerson, R. Mezrich, et al., Differences In The Attenuation Of Ultrasound By Normal, Benign And Malignment Breast Tissue, Journal of Clinical Ultrasound, Volume 4, No. 4, p. 252, 1976. Therefore, if an accurate determination of a tissue segment's attenuation coefficient could be made, it could be reliably determined whether that tissue segment is normal or contains abnormalities.

Workers in the art have not been able to measure accurately tissue attenuation coefficients by pulse echo ultrasound. Measurement of peak echo amplitudes at two different ultrasonic center frequencies by using two different transducer crystals or narrow band pass filters, as in U.S. Pat. No. 4,057,049, often yields unreliable results because other leading and trailing echoes may interfere with the echo to be analyzed and because the measurements are taken during the nonsteady-state response of the instrumentation. For a discussion of this problem, see I. Beretski, et al., Impulse Response Detection In Pulse Echo Ultrasound Recent In Vitro Experiments With A Human Aorta, Second International Symposium On Ultrasonic Tissue Characterization, National Bureau of Standards, Session 7, June 1977.

Another unsuccessful technique for accurately measuring tissue attenuation coefficients involves computing Fourier power spectrums from time segments of echo wave trains. This method yields inaccurate results because the original time segments frequently contain echoes returning from adjoining tissue segments. For a further discussion of this technique, see L. Joynt, et al., Identification of Tissue Parameters By Digital Processing of Real Time Ultrasonic Clinical Data, Second International Symposium on Ultrasonic Tissue Characterization, National Bureau of Standards, Session 8, June 1977. In the Fourier computation the spectrums are computed from the summated effect of adjacent tissues instead of just one segment. Any attempt to reduce the number of echoes to one for purposes of spectral analysis leads to the taking of shorter and shorter data segments from the output of the echo receiver. However, the true spectrum of the desired echo is modified or blurred by shortening the length of the data segment. The extent of adjacent frequencies contributing to any one point in this modified spectrum increases with decreases in the duration of the echo. Thus, there is a trade-off between axial resolution and spectral resolution in time-gated pulse echo ultrasound technique.

SUMMARY OF THE INVENTION

A novel method and apparatus is provided for accurately measuring the attenuation coefficients of a body of material through the use of pulse echo sound. In particular, the disclosed invention overcomes the problems encountered in the use of known methods of determining the attenuation coefficients of tissue segments. The present invention does not rely upon measurement of only the amplitudes of returning echoes; accordingly, the problems of variations in echo amplitudes being caused by factors other than attenuation within the tissue segment and of leading and trailing echoes interfering with the echo being analyzed are avoided. Nor does the present invention involve computing the Fourier power spectrums of the returning echoes. Such methods are inherently inaccurate because the power spectrum of relatively short echoes tends to be modified or blurred. If a longer echo is generated, the echo trains overlap and thus make inaccurate determination of the power spectrums of these echoes.

The present invention involves transmitting sonic pulses into the body of material to be analyzed until the returning echoes are white; that is, the echoes are of substantially uniform spectrum amplitude at all frequencies over a specified range. When analyzing tissue, the attenuation coefficient of a tissue segment is calculated as a function of the characteristics of the transmitted pulses which cause echoes returning from the boundaries of the tissue segment to be white. In the practice of the invention, long ultrasonic pulses may be transmitted to generate long returning echoes which tend to increase the spectral resolution of the system. In addition, axial resolution is greatly increased by the use of matched filtering analysis of the returning echoes. These techniques avoid the problems inherent in known attenuation coefficient measurement methods; namely, that high axial resolution requires low spectral resolution and high spectral resolution results in low axial resolution. With the present invention, both high axial and high spectral resolution are achieved.

In the present invention, electrical signals are created and converted into sonic pulses by a transducer. When analyzing tissue, these pulses are transmitted into the tissue segments under investigation; by analyzing the returning echoes generated by the transmitted pulses the waveshapes of pulses needed to generate white echoes from each of the tissue boundaries are determined. Generally, the pulse shape required to generate a white echo from each tissue boundary will vary for each boundary. Matched filtering conveniently can be used to determine when the echoes are white. Further, long pulses are transmitted and they generate long echoes which increase the spectral resolution of the system.

The method for determining the attenuation coefficient of a particular tissue segment involves transmitting two series of pulses into the tissue segment. A first series is transmitted until the returning echoes from the near boundary of the tissue segment of interest are white. Then a second series of transmitted pulses is transmitted until the echoes returning from the far boundary of the tissue segment under investigation are white. The attenuation coefficient of the segment is then calculated from the characteristics of the two respective pulses necessary to generate the white echoes and from the thickness of the tissue segment under investigation. The thickness of the tissue segment may be determined by any method known in the art, such as measuring the time gap between returning pulses. The attenuation coefficient can then be displayed in any traditional manner to give an indication of the composition of the tissue segment. These displays can include B- or M-mode displays. The foregoing steps are then repeated for each tissue segment for which analysis is desired.

The term "sonic" shall include the term "ultrasonic".

It is to be understood that the term white echo in this application means an a sonic pressure pulse echo which has a substantially uniform spectrum amplitude at all frequency components of the echo. Also, a high frequency matched filter shall mean a matched filter designed to respond optimally to an echo of appropriate phase characteristics and larger high frequency components of spectrum amplitude within the frequency range of the filter. A low frequency matched filter shall mean a matched filter designed to respond optimally to an echo of appropriate phase characteristic and larger low frequency components of spectrum amplitude within the frequency range of the filter.

A boundary shall mean an area within the material under analysis where there exists a change in acoustic impedance sufficient to reflect a portion of a sonic pulse. A tissue segment shall mean the material between two boundaries.

The present invention can be used to detect boundaries within any body of material and to determine the attenuation coefficients of the material between the boundaries. The present invention is particularly useful for accurate detection of abnormalities in human tissue without the need for invasive surgery.

BRIEF DESCRIPTION OF THE DRAWINGS

For a better understanding of the present invention reference may be had to the description of the preferred embodiments that follows, taken with the accompanying drawings in which.

DESCRIPTION OF THE PREFERRED EMBODIMENT

Figure 1:
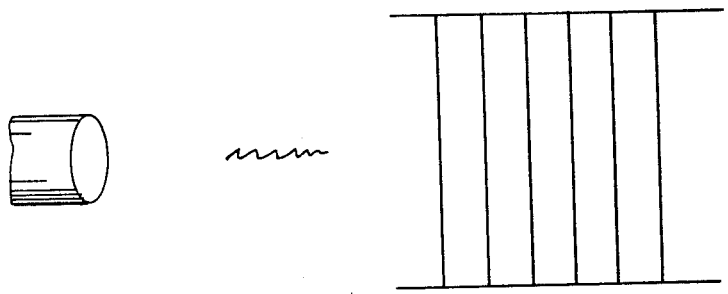
FIG. 1 is a diagrammatic view of a sonic pulse being transmitted into a body of material containing boundaries.
Figure 2:
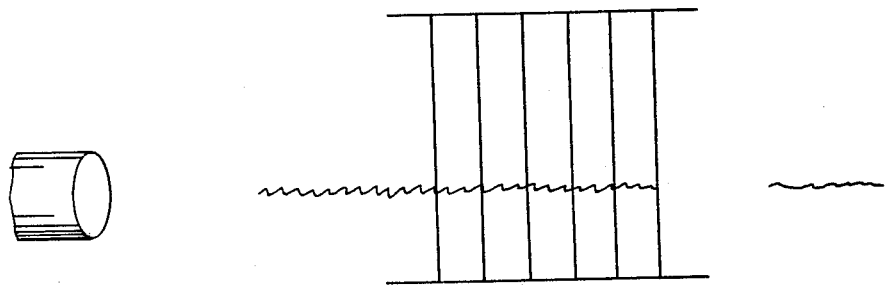
FIG. 2 is a diagrammatic view of sonic echoes returning from the boundaries of the material.
Figure 3:
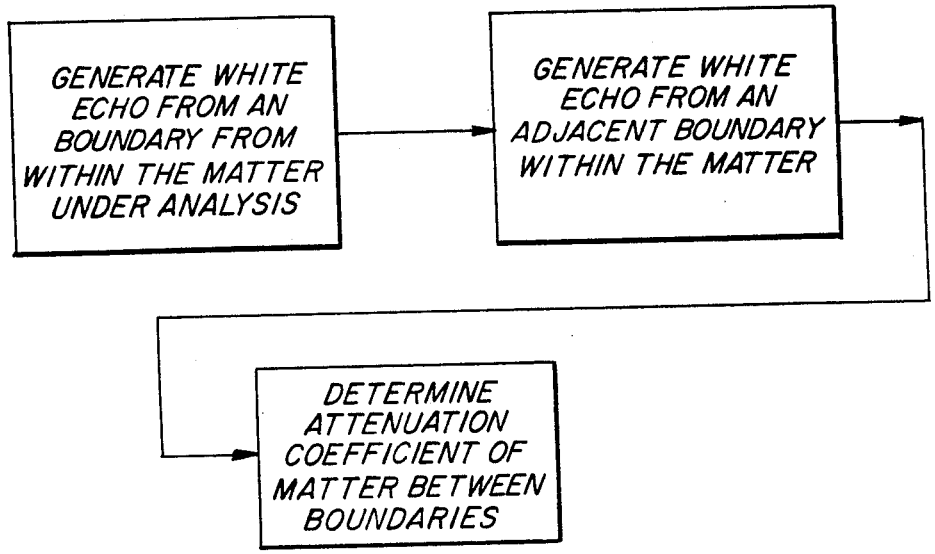
FIG. 3 is a schematic diagram illustrating a method embodying the present invention.
Figure 4:
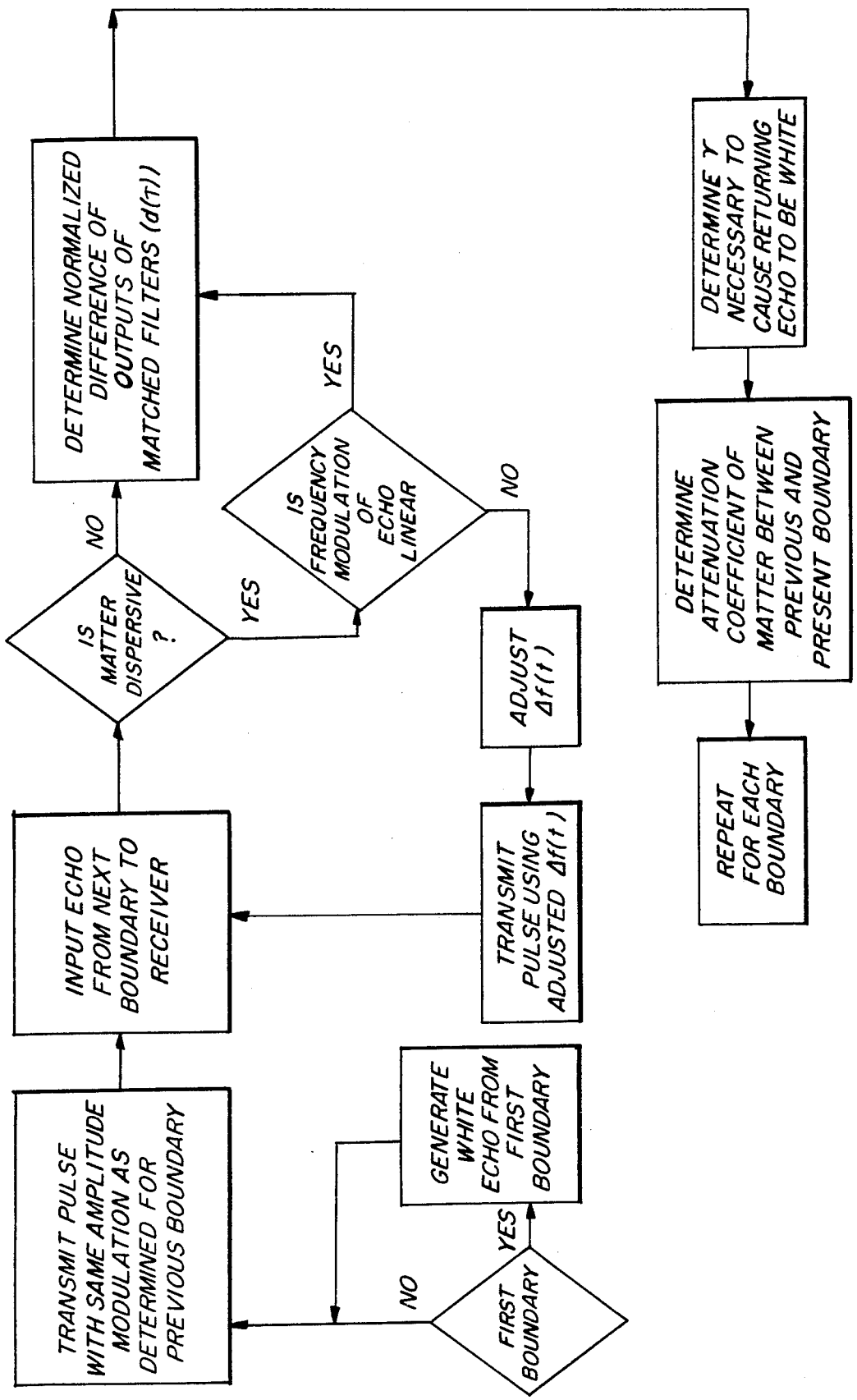
FIG. 4 is a more detailed diagram illustrating a method embodying the present invention.

Attenuation of ultrasonic pressure pulses transmitted through tissue segments for determining tissue characteristics has received considerable attention among workers in the art. Applicant himself authored a paper entitled An Iterative Real-Time Method of Estimating Biological Tissue Adsorption Coefficients In Vivo Using Pulse Echo Ultrasound, which paper is incorporated herein by reference. Attenuation within a homogeneous tissue is defined as the decrease in amplitude of the propagating ultrasonic wave due to conversion of acoustic energy to other forms of energy and due to scattering. Attenuation is defined by the following relationship:

$$\alpha(f,l) = \log_e(A_1/A_f) \qquad (1)$$

where $\alpha(f,l)$ is the attenuation and in general is a function of the propagation distance, $l$, and frequency, $f$; $A_1$ is the amplitude of the propagating ultrasonic wave at a distance, $l$, from the generating transducer; and $A_f$ is the initial amplitude of the ultrasonic wave in the medium at the site of the generating transducer.

In cases where $\alpha(f,l)$ is proportional to frequency, that is $$\alpha(f,l) = \alpha_i f l \qquad (2)$$

within the $i^{th}$ tissue segment, the proportionality constant, $\alpha_i$, is defined as the attenuation coefficient. The attenuation coefficient of a tissue segment correlates very highly with the presence or absence of abnormalities within the tissue segment. The present invention permits the accurate determination of attenuation coefficients for tissue segments and thus affords reliable determinations of tissue abnormalities without the need for invasive surgery.

Accurate real time attenuation coefficient determination can be effected by transmitting ultrasonic waves into the tissue segments and analyzing the returning echoes. The basis of the present invention is the fact that tissue geometry and transmission reflection coefficients do not modify the energy-normalized spectrum amplitude, that is spectral shape, of the echo although they do affect the signal strength of an echo. The frequency spectrum of the echo returning from the boundary of the outer tissue segment can be modeled as follows:

$$E_i(f) = S(f)H(f)ke^{-\int L\alpha(f,l)dl}e^{-j2\pi f L/v} \qquad (3)$$

where $E_i(f)$ is the spectrum amplitude of the echo returning from the $i^{th}$ boundary.

$S(f)$ is the transmitted spectrum amplitude.

$H(f)$ is the spectrum amplitude weighting of the transmitter-transducer-receiver system.

$k$ is a constant dependent on the geometry of tissue segments and product of transmission-reflection coefficients at tissue segment boundaries. $\alpha(f,l)$ is the attenuation parameter of the tissues which include both absorption, scattering and mode conversion mechanisms.

$L$ is the propagation path length of the ultrasonic wave from the piezoelectric transducer to the $i^{th}$ tissue boundary and return.

$v$ is the ultrasonic propagation velocity.

$\int L\alpha(f,l)dl$ is the total attenuation due to all tissues through which the pulse passes.

Note that of the characteristics of the tissue segments, only the attenuation parameter modifies the spectrum shape of the received echo. Thus by transmitting a pulse with a spectrum such that $$|S(f)| = g|H^{-1}(f)|e^{+\int L\alpha(f,l)dl} \qquad (4)$$

The spectral shape of the received echo from a boundary can be made white over the frequency band of the transmitted spectrum. The same process is repeated for the echoes returning from each boundary. The differences among the wave shapes of the pulses necessary to generate white echoes from each boundary represent the attenuation for each successively deeper tissue segment.

The following is a description of the preferred embodiment of the present invention and reference may be made to FIGS. 1 through 5 to enhance the understanding of this discussion. One method which embodies the present invention involves analyzing tissue by transmitting an ultrasonic pulse such that the echo returning from a boundary within the tissue is white. Another pulse is then transmitted such that the echo returning from the next spaced boundary within the tissue is white. From the characteristics of these two pulses and from the thickness of the tissue between the boundaries, the attenuation coefficient is calculated. The attenuation coefficient is displayed by any suitable method known in the art and this process is repeated for all tissue segments to be analyzed.

In cases where equation (2) accurately reflects the situation, such as where normal muscle tissue or hemoglobin is being analyzed, the integral term in equation (4) is reduced to:

$$+ \int L\alpha(f,l)dl = 2f \sum_{n=1}^{i} a_n X_n \qquad (5)$$

where the $X_n$ are the thickness of the tissue segments through which the pulse passes, the $a_n$ are the attenuation coefficients of the segments through which the pulse passes, and $i$ is the number of segments through which the pulse passes to reach the boundary which generated the echo under analysis. Equation (5) represents the total attenuation of the pulse due to all the segments through which it passes. By combining equations (3), (4), and (5) it can be seen that by generating a pulse such that:

$$|S(f)| = g|H^{-1}(f)| e^{2f \sum_{n=1}^{i} a_n X_n} \quad (6)$$

the echo returning from the appropriate boundary will be white. It follows, therefore, that if a pulse is transmitted having a shape such that:

$$|S(f)| = g|H^{-1}(f)|e^{\gamma_i f} \quad (7)$$

and if $\gamma_i$ is adjusted so that a particular returning echo is white, then $$\gamma_i = 2 \sum_{n=1}^{i} a_n X_n \quad (8)$$

It must be noted that when a relationship other than equation (2) accurately reflects the situation, that relationship can be used in equations (5) through (8) and (9) through (11) below.

Figure 10:
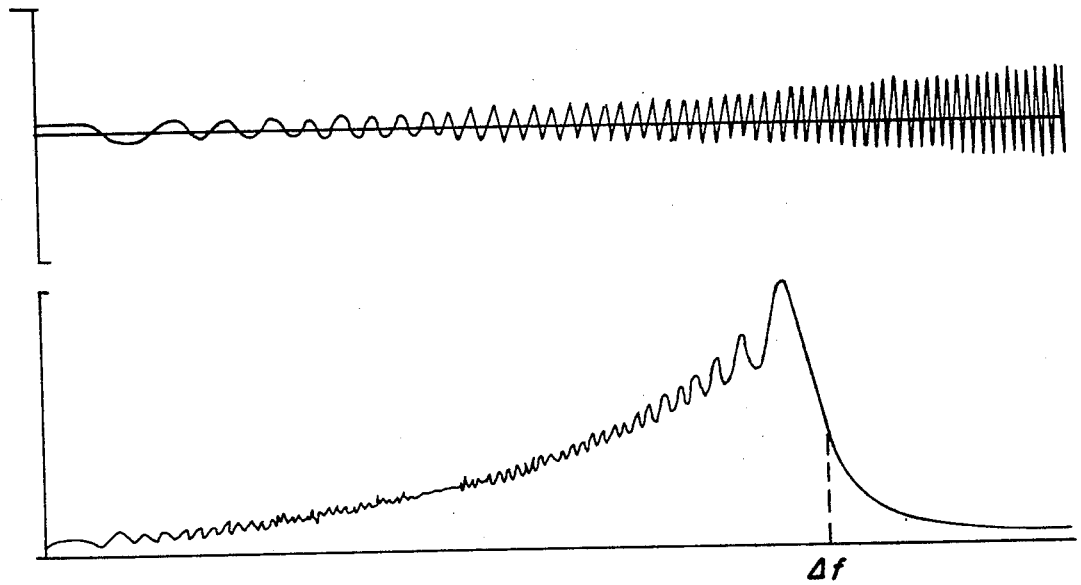

It has been known since the early days of radar that the spectrum amplitude of a swept-frequency oscillator approximates its amplitude modulation function in the time domain where the fidelity of the approximation increases as the time-bandwidth product increases. Time-bandwidth product must be larger than 50 for reasonable approximations. Therefore in yet another embodiment the transmitted pulses are of the general form:

$$S(t) = g/H^{-1}(f)|\sqrt{W(f)} \, e^{\gamma f} \sin 2\pi(\int f dt) \quad (9)$$

where g represents the gain control, $|H^{-1}(f)|$ is the transmitter-transducer receiver amplitude spectrum correction function, $\sqrt{W(f)}$ is a weighting function for improving axial resolution, f is the instantaneous frequency of the frequency modulating function where $f = f_O + \Delta f(t)$, $\Delta f(t)$ is the frequency modulating function and $\gamma$ is the quantity which is adjusted to modify the transmitted pulses and which is used to calculate the attenuation coefficient (see equation (11) below). FIG. 10 shows an example of a pulse of this form.

To calculate the attenuation coefficient for any tissue segment, it is necessary only to obtain the values of $\gamma$ necessary to cause a pulse to generate white echoes from the near and far boundaries of the tissue segment. The value of $\gamma$ necessary to cause a pulse to generate a white echo from the near boundary is shown in equation (8). The value of $\gamma$ necessary to cause a pulse to generate a white echo from the far boundary is:

$$\gamma_{i+1} = 2 \sum_{n=1}^{i+1} a_n X_n \quad (10)$$

Subtracting equation (8) from equation (9) yields:

$$\gamma_{i+1} - \gamma_i = 2a_{i+1} X_{i+1} \quad (11)$$

Solving for $a_{i+1}$ the attenuation coefficient of the tissue segment yields:

$$a_{i+1} = \gamma_{i+1} - \gamma_i / 2 X_{i+1} \quad (12)$$

$X_{i+1}$ is the thickness of the tissue segment and may be determined by any method known in the art such as determining the time between the echoes returning from the near and far boundaries of the tissue segment.

Where the tissue to be analyzed is non-dispersive in nature, $\Delta f(t)$ is equal to Bt, where B is the rate of change in the frequency of the frequency modulating function with respect to time. Non-dispersive tissues are those in which ultrasonic propagation velocity is independent of frequency. In dispersive tissues, that is, those in which the ultrasonic propagation velocity is dependent on frequency, $\Delta f(t)$ can be approximated by the following expression:

$$\Delta f(t) = \Delta f'(0)t + \Delta f''(0)(t^2/2) \quad (13)$$

In practice, prior to adjusting the transmitted pulse to generate a white echo, $\Delta f(0)$ and $\Delta f'(0)$ are adjusted such that the echoes returning from the appropriate boundaries are frequency modulated linearly, by maximizing the output of a high frequency matched filter due to the input of the echo by any known algorithm such as the "steepest descent" algorithm. In the method involving transmission of a pulse having a waveform of a shape described by equation (9) above, the transmitted pulses are adjusted by modifying $\gamma$ until the echoes returning from the appropriate boundaries are white.

To determine whether a returning echo is white, the echo is converted to an electrical signal and input to a pair of matched filters. The matched filters can be such that $$|H_H(f)| = |H_L(\Delta f - f)| \quad (14)$$

where $|H_H(f)|$ is the spectrum amplitude of the impulse response for the high frequency matched filter and $|H_L(f)|$ is the spectrum amplitude of the impulse response for the low frequency matched filter. Normalized differences of the outputs of the matched filters will be zero when the returning echo is white. The normalized difference of the matched filters is defined by $$d(\tau) = [r_L(\tau) - r_H(\tau)] / [r_L(\tau) + r_H(\tau)] \quad (15)$$

where $d(\tau)$ is the normalized difference of the matched filters, $r_L(\tau)$ is the peak output of the low frequency matched filter and $r_H(\tau)$ is the peak output of the high frequency matched filter. If the normalized difference is positive, the value of $\gamma$ for the next transmitted pulse must be increased and if the normalized difference is negative, the value of $\gamma$ for the next transmitted pulse must be decreased. When a normalized difference of zero is obtained the returning echo generated by that pulse is white.

Figure 8:
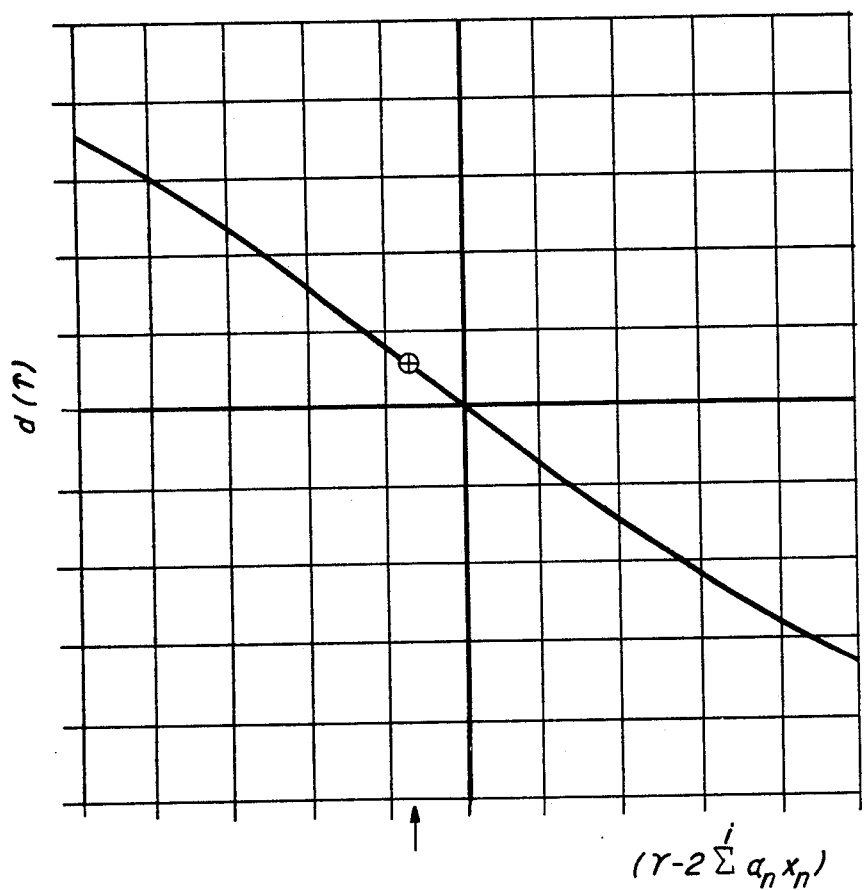
FIG. 8 is a plot of the normalized difference of the outputs of the matched filters versus the quantity $$(\gamma_i - 2\sum^{i} a_n X_n)\Delta f;$$
Figure 9:
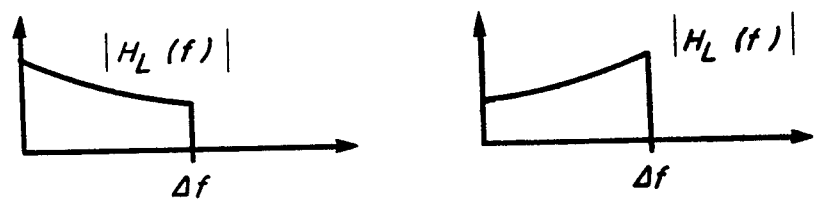
FIG. 9 is a plot of the Fourier spectrum amplitude of matched filters impulse responses capable of use in the present invention; and, FIG. 10 is a computer-generated plot of a transmitted pulse and the spectrum amplitude of that pulse.

In an alternate and preferable embodiment after calculating the attenuation coefficient of the first tissue segment, only one pulse need be transmitted for each additional tissue segment to determine each segment's attenuation coefficient. It can be noted from equations (3) and (9) that when $\gamma$ equals $\int a(f,l)dl$, the returning echo is white. Since the normalized differences of the output of the matched filters and $(\gamma - \int a(f,l)dl)$ will both be zero when the echo returning from a given boundary is white a plot of the normalized difference versus $(\gamma - \int a(f,l)dl)$ will give an indication of how $\gamma$ must be modified for a given normalized difference such that the next transmitted pulse would yield a white echo from that boundary. FIG. 8 shows such a plot where attenuation is linearly dependent upon frequency. This expression is shown in equation (2) and reduces the integral term to $$2f \sum_{n=1}^{i} a_n X_n \quad (16)$$

where $X_n$ is the propagation path length to the boundary of the tissue segment being analyzed and $a_n$ is the attenuation coefficient of that segment. This relationship is particularly appropriate when the tissue being analyzed is normal muscle or hemoglobin. The behavior of the normalized difference of the two matched filters' peak outputs for the echo in response to varying γ has been simulated on a digital computer using Fortran as the applications program language and a vender supplied discrete (fast) Fourier transform subroutine. Plots similar to that shown in FIG. 8 may be generated by computer modeling by those of ordinary skill in the art where it is determined that the tissue segments are such that the attenuation coefficient is not linearly proportional to the frequency. It should be noted that the plot in FIG. 8 is linear in the operating range of the present invention. Therefore, only one pulse need be transmitted to determine the shape of a transmitted pulse necessary to produce a white echo from that boundary when the shape of a pulse necessary to generate a white echo from an adjacent boundary is known. When a pulse is transmitted and reflected from a particular boundary and a normalized difference is calculated, the appropriate γ to cause the normalized difference to equal zero can be calculated from FIG. 8. Therefore to determine the appropriate γ to cause a white echo to be generated from a given boundary it is necessary to generate a white echo from the near boundary of the first tissue segment to be analyzed using the techniques described above. Then, this same pulse is used to generate an echo from the next adjacent (nearer or farther) boundary. By using the relationship $$\gamma_{new} = \gamma_{old} + d(\tau_i)/0.08 \, \Delta f \qquad (17)$$

the value of γ necessary to generate a white echo from the adjacent boundary can be calculated, where $\gamma_{new}$ is the value of γ necessary to generate a white echo from the adjacent boundary, $\gamma_{old}$ is the value of γ of the pulse most recently transmitted, $d(\tau_i)$ is the computed normalized difference and $\Delta f$ is the frequency bandwidth of the transmitted pulse. Obviously, if an echo is to be analyzed from the next nearer adjacent boundary, the $d(\tau_i)/0.08 \, \Delta f$ term is subtracted from rather than added to $\gamma_{old}$ in equation (17). The two values of γ, $\gamma_{old}$ and $\gamma_{new}$, are then used to calculate the attenuation coefficient of the first segment using equation (11). To calculate the attenuation coefficient of the next adjacent boundary, it is necessary to calculate one more value of γ. $\gamma_{new}$ for the old segment is used as the value of $\gamma_{old}$ for the new segment. $\gamma_{new}$ for the new segment is determined by transmitting a pulse having the value of $\gamma_{old}$ for its value of γ, calculating the normalized difference, and substituting these values into equation (17). The value of $\gamma_{new}$ of this segment is used for the value of $\gamma_{old}$ for the next adjacent segment. This process is repeated until all segments are analyzed.

Figure 5:
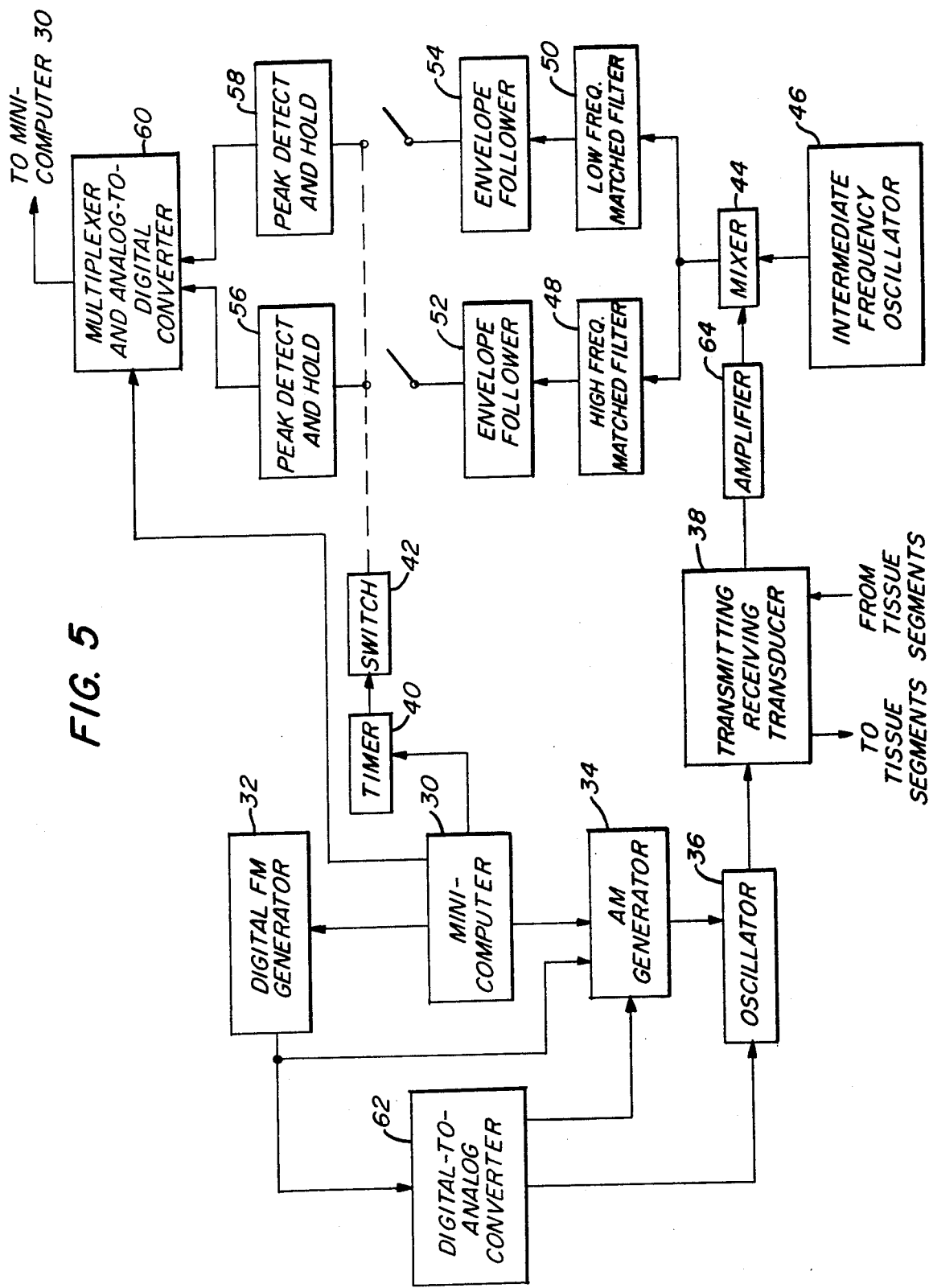
FIG. 5 is a schematic diagram of apparatus embodying the present invention.
Figure 6:
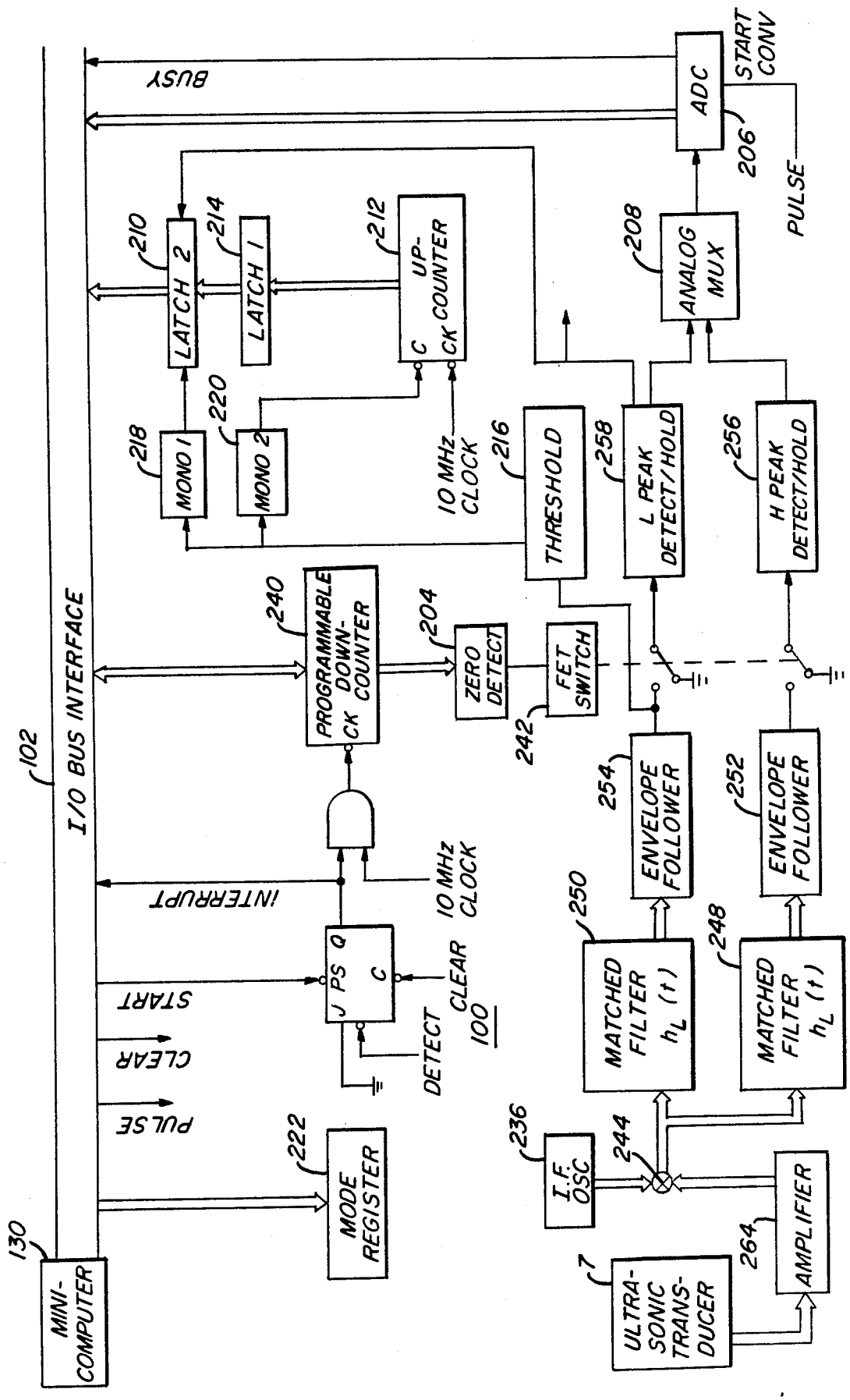
FIG. 6 is a schematic diagram of a receiver capable of use in the present invention.
Figure 7:
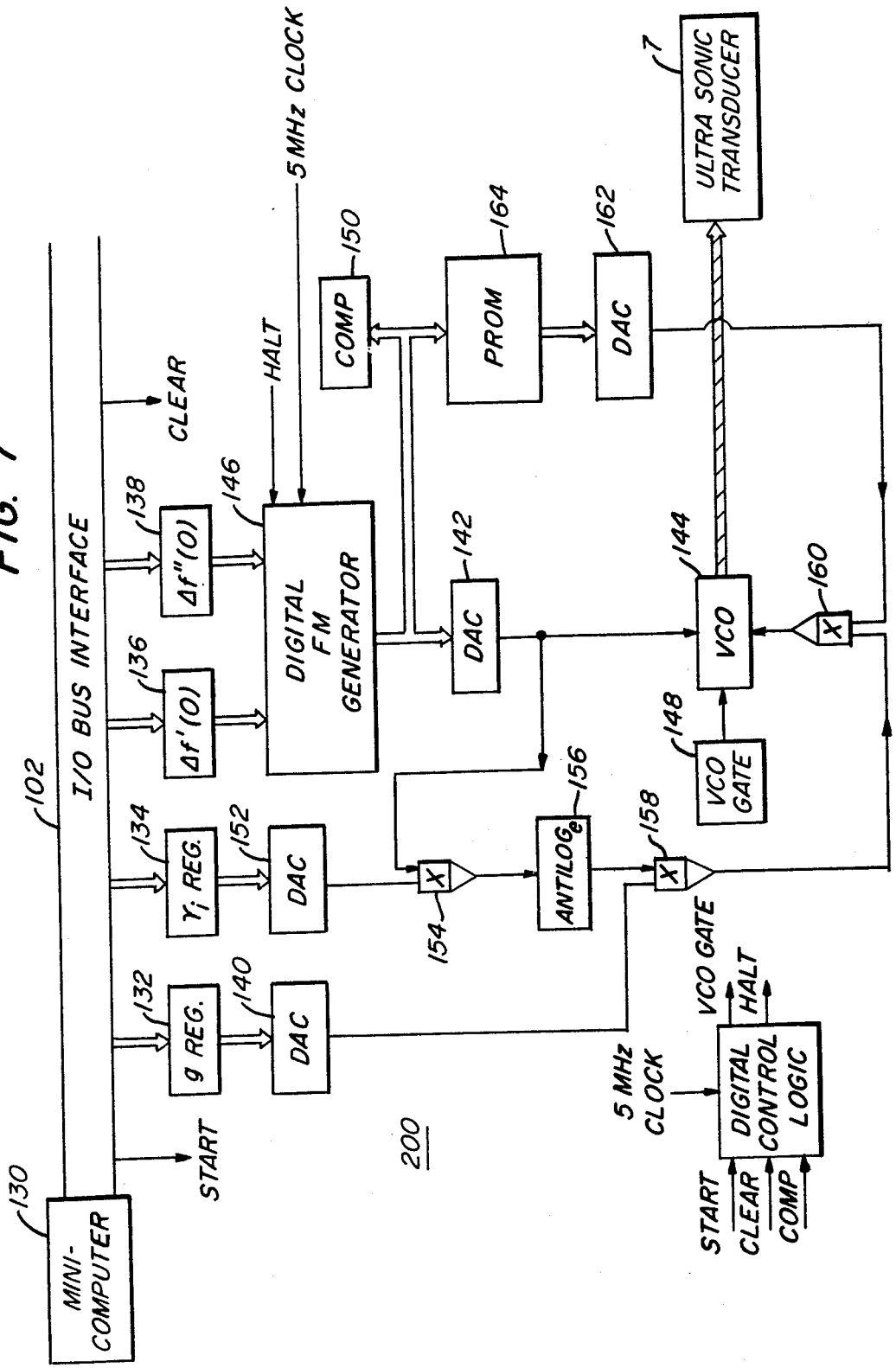
FIG. 7 is a schematic diagram of a transmitter capable of use in the present invention.

Any commercial minicomputer, such as Data General Corporation's NOVA 3/D can be used to calculate the parameters of the electrical signal that will be converted to an ultrasonic pulse and transmitted into the tissue segments and to control the sequence of operations of the present invention by appropriate known computer control and programming techniques. The same minicomputer can include a software switch which can be used to indicate whether the tissue to be analyzed is dispersive. The parameters of the signal can be input to any electrical circuit appropriate for creating the electrical signal. Examples of such circuitry is depicted in FIGS. 5, 6 and 7. In FIG. 5, the minicomputer 30 calculates the parameters of the next electrical signal to be created. From these parameters, the FM generator 32 and the AM generator 34 create the amplitude and frequency modulating functions. The outputs of the generators 32 and 34 are fed into oscillator 36. Oscillator 36 can be any appropriate oscillator such as a Tektronix FG504. The output of the oscillator 36 after modulation by the transmitting transducer represents the waveform shape of the ultrasonic pulse that will be transmitted. The output of the oscillator 36 is input to the transmitting/receiving transducer 38 which converts the signal to an ultrasonic pulse and directs the pulse into the tissue segments under analysis. Echoes returning from the tissue segments are also input to the transducer 38. A timer 40 activates the switch 42 when the echo to be analyzed reaches the transducer 38. The timer 40 can be a programmable down-counter loaded with an interval of time equal to the propagation time of a pulse traveling to and returning from a given tissue segment boundary. The switch 42 can be a field effect transistor. The transducer 38 converts the echo to an electrical signal and this signal is amplified by amplifier 64 and input to a mixer 44 along with the output of an intermediate frequency oscillator 46. The operating frequency of the intermediate frequency oscillator 46 is substantially the same as the center frequency of the matched filters 48 and 50. The output of mixer 44 is input to matched filters 48 and 50. The outputs of filters 48 and 50 are input to envelope followers 52 and 54 respectively. Followers 52 and 54 track the envelope of the outputs of filters 48 and 50. The outputs of envelope followers 52 and 54 are input to peak detect and hold circuits 56 and 58, respectively. Circuits 56 and 58 detect the peak outputs of matched filters 48 and 50. These peak outputs are converted to digital signals by analog-to-digital converter 60 and input to the minicomputer 30. Minicomputer 30 computes the normalized difference of the outputs of filters 48 and 50 and calculates the parameters of a pulse which, when transmitted, will generate a white echo from the boundary under examination.

Reference may be made now to FIGS. 6 and 7 which show embodiments of a transmitter 200 and receiver 100 of the present invention. The apparatus depicted in FIG. 7 is used to generate the electrical signal which is converted into an ultrasonic pulse by the transducer. Control of the transmitter and receiver for the appropriate sequencing of operations is achieved through the use of a programmed general purpose digital minicomputer 130. The transmitter, receiver and focusing circuitry accept and provide data and command signals from and to the minicomputer 130 via its digital input/output bus 102.

For each pulse transmitted, minicomputer 130 first updates the contents of the g, $\gamma_i$, $\Delta f'(0)$ and $\Delta f''(0)$ registers, 132, 134, 136 and 138 respectively, as necessary. Each register's contents is in the digital form of 16 bit binary words. The output of the Digital FM Generator after the START command is a binary number, $\Delta f(t)$, which is a general quadratic function of time where $$\Delta f(t) = \Delta f'(0)t + \frac{\Delta f''(0)t^2}{2}, \qquad (18)$$

and after its conversion to an analog voltage by its digital-to-analog converter, DAC, 142, $\Delta f(t)$ is used to frequency modulate, FM, the voltage controlled oscillator, VCO, 144, as well as generate the amplitude modulation, AM, function input to VCO 144. The binary contents of registers 136 and 138 as loaded by minicomputer 130 determine the initial slope and second derivative of the general quadratic function, $\Delta f(t)$. When the system is used to interrogate biological tissues in which ultrasonic velocity dispersion is insignificant, the content of $\Delta f'(0)$ register 136 is always equal to the chirp rate, B, used in designing the matched filters for the receiver and the content of the $\Delta f''(0)$ register 138 is always zero. Under these conditions the output of Digital FM Generator 146, $\Delta f(t)$, is a linear function of time and the output of its digital-to-analog converter, DAC 142, is a linear voltage ramp. VCO GATE signal 148 is a digital switching signal which turns "ON" the output from VCO 144. VCO GATE 148 goes "ON" at the beginning of the START command and goes "OFF" again when signaled by comparator circuit 150 that $\Delta f(t)$ has reached its upper frequency band width. The output of comparator 150, COMP, is also used for generating the HALT signal to stop Digital FM Generator 146. As previously mentioned the process of generating the amplitude modulation AM, input to VCO 144 also uses the analog voltage format of $\Delta f(t)$. The digital binary contents of $\gamma_i$ register 134 are converted to analog voltage format by its DAC 152 and the product of $\gamma$, and $\Delta f(t)$ is formed by analog voltage multiplier module 154. This product is exponentiated, that is converted to $e^{\gamma_i \Delta f(t)}$, by analog voltage antilogrithm module 156. The binary content of g register 132, which is the means by which the minicomputer 130 effects gain control, is converted to analog format by DAC 140 and analog voltage multiplier module 158 forms the product, $ge^{\gamma_i \Delta f(t)}$. The final product and amplitude modulation input to VCO 144 is formed by analog voltage multiplier module 160 from the volage corresponding to $ge^{\gamma_i \Delta f(t)}$ and the voltage output from DAC 162 which is proportional to the binary contents of programmable read-only memory 164, PROM, for a given input address of $\Delta f(t)$. PROM 164 is originally altered from its manufactured blank state such that the binary content of each address, $\Delta f(t)$, is a digital, 8-bit binary word that is proportional to the product $$|H^{-1}(f)|\sqrt{W(f)} \tag{19}$$

where
- $|H^{-1}(f)|$ is the transmitter-transducer-receiver spectrum amplitude correction function originally mentioned in equation (2);
- $\sqrt{W(f)}$ is the square root of the Hamming weighting function, $W(f) = 0.54 - 0.46 \cos(2\pi f/\Delta f)$, to eliminate interference from sidelobes in the output of the matched filters; and,
- $f = f_o + \Delta f(t)$ where $f_o$ is the low frequency band limit of 1 MHz and $\Delta f(t)$ is the frequency modulation.

The correction function is experimentally derived by observing the uncorrected system's spectrum amplitude of an echo returning from a specular reflector such as a steel ball bearing suspended in a small water bath.

The block diagram of receiver 100 is shown in FIG. 6. Before the START command is given to both transmitter 200 and receiver 100 by the minicomputer 130, the Programmable Down-Counter 240 is loaded with the number of 100-nanosecond intervals equal to the sum of the estimated round-trip delay of the $i^{th}$ echo plus the pulse duration. At the START command the Programmable Down-Counter begins counting at a 10 MHz rate toward zero. When the count reaches zero, zero detect 204 sets analog field-effect transistor 242, FET, switches connecting the outputs of Envelope Followers 252 and 254 to Peak Detect/Hold circuits 256 and 258. Note that the echoes returning to receiving transducer 7 generate signals which are amplified by amplifier 264 and mixed with the output of intermediate frequency oscillator 236, I.F.OSC, which operates at the center frequency of surface acoustic wave matched filters 248 and 250. The output of mixer 244 is fed to matched filters 248 and 250 characterized by their impulse responses $h_L(t)$ and $h_H(t)$, where $$h_L(t) = e^{-2x/T}\sqrt{0.54-0.46\cos(2\pi t/T)}\sin(2\pi(f_o+Bx/2)x)$$

$$h_H(t) = e^{2(x-T)/T}\sqrt{0.54-0.46\cos(2\pi t/T)}\sin(2\pi(f_o+Bx/2)x)$$

where
- $x = T - t$
- $T = 50 \ \mu sec$
- $\Delta f = 5$ MHz
- $B = \Delta f/T = 0.1$ MHz $\mu sec^{-1}$
- $f_o = f_{IF\ OSC} + 1$ MHz $= 71$ MHz The outputs of the matched filters 248 and 250 are processed by Envelope Followers 252 and 254 which extract and output to Threshold and Peak Detect/Hold circuits 256 and 258 the envelope of matched filters 248 and 250 outputs. Programmable Down-Counter 250 continues counting until the echo's peak is detected as indicated by zero DETECT 204. When the peak is detected the minicomputer's 130 interrupt bus is signaled. The minicomputer 130 then initiates a conversion on the held analog voltage output of H Peak Detect-/Hold 256 by analog-to-digital converters ADC 206. When the conversion is finished the contents of ADC 206 are read into the minicomputer 130 and another conversion is initiated on the held analog voltage output of L Peak Detect/Hold circuit 258. Upon completion of the conversion the contents of ADC 206 are again read into the minicomputer 130. Thus the analog voltages of peak holding circuits 256 and 258 corresponding to $r_L(\tau_i)$ and $r_H(\tau_i)$ are sequentially converted to 12 bit binary words and acquired by the minicomputer 130 in preparation for computing the normalized difference, $d(\tau_i)$. The appropriate peak detect/hold circuit's, 256 or 258, output is selected for conversion by analog multiplexer 208, MUX, as directed by bit $\phi$ of minicomputer 130 loaded Mode register 222.

The time elapsed between the START command and the time of detection of the peak of the $i^{th}$ echo is derived by adding the initially loaded contents of Programmable Down-Counter 240 and the negative value of its current contents after the $i^{th}$ peak has been detected. An echo coming from the adjacent tissue interface farther from transducer 7 may be captured by peak detection circuits 256 and 258 with the next pulse generated by initially loading the contents of Programmable Down-Counter 240 with a value equal to four greater than the elapsed time between the START command and the detection of the $i^{th}$ echo's peak. This added value is approximately equal to the time necessary for a pulse to completely pass through a given point. An echo coming from the adjacent tissue interface nearer transducer 7 may be captured by peak detection circuits 256 and 258 with the next pulse generated by initially loading the contents of the Programmable Down-Counter 240 with a value equal to the elapsed time between the START command and the peak of the $i^{th}$ echo minus the contents of Latch2 210 minus 4 additional counts.

The Up-Counter 212, Latch1 214 and Latch2 210 function to provide an estimate of the time elapsed between the previous and current echo. When Threshold detector 216 detects the beginning of an echo, the contents of counter 212 is held in Latch1 214 and counter 212 is reinitialized to zero by the outputs of MONO1 218 and MONO2 220. Counter 212 immediately restarts and continues until another echo exceeds the threshold of Threshold Detector 216. If Peak Detect/Hold circuits 256 and 258 detect a peak, the contents of Latch1 214, are held in Latch2 210 so that the count is not lost when the output of MONO1 218 returns to its quiescent state.

A method for determining the attenuation coefficients of a series of adjacent tissue segments beginning with the nearest segment and progressing through deeper segments to the deepest segment embodying the present invention comprises the steps of:

a. Generate an electrical pulse of the form $s(t) = g|H^{-1}(f)|e^{\gamma f}\sqrt{W(f)} \sin 2\pi \int f dt$ where $f = f_0 + \Delta f(t)$, and where $W(f)$ can be the Hamming function and $\Delta f(t)$ can be equal to $Bt$ when examining non-dispersive tissue and where $\Delta f(t)$ can be equal to $$\Delta f'(0)t + \Delta f''(0)\frac{t^2}{2}$$

when examining dispersive tissue. This pulse may be generated by any means known to those of ordinary skill in the art and can include a commercial minicomputer and apparatus depicted in FIG. 7.

b. Convert the electrical pulse generated in step (a) into an ultrasonic pressure pulse and direct the ultrasonic pulse into the tissue under analysis. This conversion may be effected using any appropriate wideband transducer known in the art.

c. Wait until the echo of the transmitted ultrasonic pulse returns to the receiver from the near boundary of the nearest tissue segment to be analyzed. This step can be effected using a timer that is integral to the microcomputer. At the same time step a. is begun, the timer is set to the sum of the time necessary to perform steps (a) and (b), the time required for the ultrasonic pulse to travel to the near boundary of the first tissue segment, and the time necessary for the echo to return to the transducer from the near boundary of the first tissue segment. When the timer reaches zero, a switch, which switch can be a field-effect transistor, FET, is closed, thereby alowing the next echo, which echo will be the echo of interest, to enter the receiver. The timer can be a programmable down-counter which is integral with the minicomputer. After each echo is analyzed the switch is opened and the timer is set to allow the next echo of interest to be analyzed.

d. Convert the echo from the near boundary of the nearest tissue to an electrical signal via an ultrasonic transducer. This transducer can be the same transducer used in step (b) or it can be a distinct transducer appropriate for converting the received echoes into electrical signals.

e. Electrically mix the output of an intermediate frequency oscillator with the amplified signal generated in step (d).

f. Input the signal generated in step e. to a pair of matched filters, one being a high frequency matched filter and the other being a low frequency matched filter, having a center frequency equal to the operating frequency of the intermediate frequency oscillator. The high and low frequency matched filters may have spectrum amplitudes of their impulse responses such that $|H_H(f)| = |H_L(\Delta f - f)|$ where $|H_H(f)|$ and $|H_L(f)|$ correspond respectively to the high and low frequency matched filters' impulse responses.

g. Check the output of the high frequency matched filter to determine if the returning echo is frequency modulated linearly only if the tissue under analysis is dispersive. The returning echo is frequency modulated linearly when the output of the high frequency matched filter is maximum. The frequency modulation function of the transmitted pulse is adjusted, a pulse modulated by the adjusted frequency modulation function is transmitted, and the output of the high frequency filter is checked to determine if it is maximum. This adjustment of the frequency modulation function and transmission of the adjusted pulse is continued until the output of the high frequency matched filter is maximum. The frequency modulation function can be adjusted and the output of the high frequency matched filter can be maximized by adjusting $\Delta f'(0)$ and $\Delta f''(0)$ according to any known method, such as the steepest descent method.

h. Determine whether the returning echo is white after step (f) if the tissue is non-dispersive or after step (g) if the tissue is dispersive. This is effected by computing the normalized difference of the output of the matched filters according to the expression $d(\tau) = [r_L(\tau) - r_H(\tau)]/[r_L(\tau) + r_H(\tau)]$ where $d(\tau)$ is the normalized difference, $r_L(\tau)$ is the peak output of the low frequency matched filter and $r_H(\tau)$ is the peak output of the high frequency matched filter. The peak outputs of the matched filters can be determined by inputting these outputs into a pair of any appropriate known envelope follower circuits. The outputs of the envelope followers are input to a pair of any appropriate known peak detect and hold circuits. The outputs of the peak detect and hold circuits represent the peak outputs of the matched filters. The minicomputer calculates the normalized difference from these peak values. When the normalized difference equals zero, the returning echo is white.

i. Adjust the amplitude modulation function open the switch, set the timer to analyze an echo returning from the same boundary, and transmit a new pulse. Repeat this process until the normalized difference is zero. Reopen the switch and set the timer so as to allow an echo from the next farthest boundary to be received. The amplitude modulation function can be adjusted by adjusting the value of $\gamma$. If the normalized difference is positive, $\gamma$ is increased. If the normalized difference is negative, $\gamma$ is decreased. Any method known in the art may be used to minimize the number of iterations necessary to generate a white ehco.

j. Transmit a pulse with the amplitude modulation function of the pulse which generated a white echo from the near boundary in step h.

k. Receive the echo returning from the far boundary of the nearest tissue segment to be analyzed and determine whether the echo is white in the same manner as in steps (c) through (h) above. To capture the echo from the far boundary, an amount of time is loaded into the timer equal to the amount loaded in step (c) plus the time necessary for an echo to pass a given point. This ensures that the next echo received will be the echo from the far boundary instead of the near boundary. However, when determining the amplitude modulation functions of pulses necessary to generate white echoes from all but the initial boundary, it is only necessary to transmit one pulse per boundary. In general, the value of $\gamma$ necessary to cause a transmitted pulse to generate a white echo from a particular boundary can be calculated using a plot generated by a computer of the normalized difference of the outputs of a matched filters versus $\gamma$ minus the total attenuation of the pulse due to its travel through the tissue to the boundary in question and back to the receiver. In the case where attentuation is linearily dependent upon frequency, the total attenuation is $$2f \sum_{n=1}^{i} a_n X_n.$$

The plot, therefore, can be a plot of $d(\tau_i)$ versus $$(\gamma_i - 2f \sum_{n=1}^{i} a_n X_n).$$

This plot is linear in the operating region of the system after the first white echo is obtained from the first boundary. In one case therefore, $\gamma$ can be calculated using the plot in FIG. 8. The impulse responses of the matched filters used in the system upon which FIG. 8 is based are $$h_L(t) = e^{-2(x)/T}\sqrt{0.54 - 0.46 \cos(2\pi t/T)} \sin(2\pi(f_o + Bx/2)x)$$

and $$h_H(t) = e^{-2(X-T)/T}\sqrt{0.54 - 0.46 \cos(2\pi t/T)} \sin(2\pi(f_o + Bx/2)x)$$

where $h_L(t)$ is the impulse response of the low frequency matched filter and $h_H(t)$ is the impulse response of the high frequency matched filter. Based on FIG. 8, $\gamma$ can be calculated from the expression for the linear region of the past, $\gamma = \gamma' + d(\tau)/0.08\Delta f$, where $\gamma$ is the value of $\gamma$ necessary to cause a white echo to be generated from the boundary in question, $\gamma'$ is the value of $\gamma$ necessary to cause a white echo to be generated from the next nearest boundary, $d(\tau)$ is the normalized difference of the outputs of the matched filters due to an input of the echo returning from the boundary in question generated by a pulse having $\gamma'$ as its value of $\gamma$, and $\Delta f$ is the frequency range of the transmitted pulse. Therefore, given the value of $\gamma$, $\gamma'$, for the first boundary, the value of $\gamma$ for the next farthest boundary can be determined by reopening the switch, setting the timer such that a pulse from such next farthest boundary can be analyzed, transmitting a pulse with the value of $\gamma'$ for its value of $\gamma$, determining $d(\tau)$ corresponding to the echo returning from such next farthest boundary, and using the above equation to compute the $\gamma$ required to cause a white echo to be generated from such next farthest boundary. At this point, the values of $\gamma$ corresponding the the boundaries on each side of the first tissue segment are known.

1. Determine the attenuation coefficient of the first tissue segment. This determination can be made using the expression $a_j = (\gamma_j - \gamma_i)/2X_j$, where $a_j$ is the attenuation coefficient of the first tissue segment, $\gamma_j$ is the value of $\gamma$ corresponding to the far boundary of the first tissue segment, $\gamma_i$ is the value of $\gamma$ corresponding to the near boundary of the first tissue segment, and $X_j$ is the thickness of the first tissue segment. $X_j$ can be determined using any method known in the art such as measuring the time difference between echoes returning from the near and far boundaries of the first tissue segment.

m. Determining the attenuation coefficients for all tissue segments to be analyzed in a manner similar to that outlined in steps (j), (k), and (l) above. It is necessary only to use steps (j), (k) and (l) because only the value of $\gamma$ necessary to cause a white echo to be generated from the far boundary of each segment need be determined. The value of $\gamma$ for the far boundary of the tissue segment for which an attenuation coefficient was just determined is used as the value of $\gamma'$ for the new tissue segment.

In another embodiment, the initial segment analyzed is that segment farthest from the transducer and progressively nearer segments are analyzed until the nearest has been analyzed.

In yet another embodiment, an entire volume of tissue is analyzed by analyzing progressively deeper tissue segments and then analyzing progressively nearer tissue segments along a parallel return path and repeating this pattern throughout the tissue volume.

What is claimed is:

1. A method for determining the attenuation coefficient of a tissue segment comprising the steps of:
   a. transmitting into said tissue segment a first ultrasonic pressure pulse such that the echo returning from a first boundary within said tissue segment is white;
   b. transmitting into said tissue segment a second ultrasonic pressure pulse such that the echo returning from a second boundary within said tissue segment is white;
   c. determining the attenuation coefficient of said tissue segment as a function of said transmitted pulses and the thickness of said tissue segment.

2. The method claimed in claim 1 wherein the steps of transmitting said ultrasonic pulses comprise:
   transmitting into said tissue segment a first series of ultrasonic pressure pulses until a white echo is detected, the shape of each pulse in said series being different from the shape of the immediately previous pulse in said first series of pulses.

3. The method claimed in claim 1 wherein the steps of transmitting said ultrasonic pulses comprise:
   transmitting an ultrasonic pulse into said tissue segment;
   determining whether the echo returning from the appropriate boundary of said tissue segment is white;
   modifying the shape of said pulse; and,
   repeating the three previous steps until said returning echo is white.

4. The method claimed in claim 3 wherein the steps of transmitting an ultrasonic pulse comprise:
   creating an electrical signal having the form $$S(t) = g|H^{-1}(f)|\sqrt{W(f)}e^{\gamma f} \sin 2\pi \int f dt$$

where g is the system gain control,
   $|H^{-1}(f)|$ is the transmitter-transducer-receiver spectrum amplitude correction function,
   $\sqrt{W(f)}$ is a weighting function for improving axial resolution,
   f is the instantaneous frequency of the frequency modulating function and is equal to $f_o + \Delta f(t)$,
   $f_o$ is the initial frequency value of the frequency modulating function, and Δf(t) is a general function of time.
converting said electrical signal into an ultrasonic pulse of the same form; and,
directing said ultrasonic pulse into said tissue segments.

5. The method claimed in claim 4 wherein:

$$\Delta f(t) = \Delta f'(O)t + \Delta f''(O)\frac{t^2}{2},$$

where Δf'(0) is the first derivative of Δf(t) with respect to time at t=0 and Δf''(0) is the second derivative with respect to time of Δf(t) at t=0.

6. The method claimed in claim 4 wherein $$\Delta f(t) = Bt,$$

where B is the rate of change in frequency of f; and wherein
W(f) is the Hamming function, and $$W(f) = 0.54 - 0.46 \cos(2\pi f/\Delta f).$$

7. The method claimed in claim 5 wherein the steps of determining whether said echoes are white comprise:
converting into an electrical signal the echo returning from the appropriate boundary of said tissue segment;
introducing said electrical signal into a pair of matched filters;
computing the normalized difference of the outputs of said matched filters; and,
comparing said normalized difference to zero, said normalized difference being substantially zero when the input to said matched filters is white.

8. The method claimed in claim 7 wherein said matched filters comprise:
a high frequency matched filter; and,
a low frequency matched filter such that $$|H_H(f)| = |H_L(\Delta f - f)|,$$

where $|H_H(f)|$ is the Fourier spectrum amplitude of the impulse response of said high frequency filter and $|H_L(f)|$ is the Fourier spectrum amplitude of the impulse response of said low frequency filter, and Δf is the operating frequency range of said matched filters.

9. The method claimed in claim 8 wherein said normalized differences are computed by using the following equation:

$$d(\tau) = [r_L(\tau) - r_H(\tau)]/[r_L(\tau) + r_H(\tau)]$$

where d(τ) is the normalized difference of the outputs of the matched filters, $r_H(\tau)$ is the peak output of said high frequency filter and $r_L(\tau)$ is the peak output of said low frequency filter.

10. The method claimed in claim 2 further comprising the steps of:
transmitting into said tissue segment, prior to transmitting each of said series of pulses, an initial series of ultrasonic pressure pulses until the echo returning from the boundary under analysis is frequency modulated linearly.

11. The method claimed in claim 4 wherein the attenuation coefficient of said tissue segment is computed using the following equation:

$$\alpha_j = (\gamma_j - \gamma_i)/2X_j,$$

where $\alpha_j$ is the attenuation coefficient of said tissue segment, $\gamma_i$ and $\gamma_j$ are the values of γ in the expression describing the pulses of said series of pulses which cause a white echo to return from the near boundary of said tissue segment and which cause a white echo to return from the far boundary of said tissue segment and $X_j$ is the thickness of said tissue segment.

12. A method of detecting abnormalities in a tissue segment comprising the steps of:
a. transmitting an amplitude and frequency modulated ultrasonic pulse into said tissue segment;
b. adjusting said frequency modulation of said pulse and transmitting said adjusted pulse into said tissue segment if said tissue segment is dispersive and if the echo returning from the near boundary of said tissue segment is not frequency modulated linearly;
c. repeating steps (a) and (b) until an echo is received from said near boundary which is frequency modulated linearly, if said tissue segment is dispersive;
d. adjusting the amplitude modulation of said pulse and transmitting said adjusted pulse into said tissue segment if said echo received in step (c) is not white;
e. repeating step (d) until said echo returning from said near boundary is white;
f. transmitting an ultrasonic pulse into said tissue segment, said pulse having substantially the same waveshape as the pulse which caused a white echo to be generated from said near boundary;
g. determining from the spectrum amplitude of the echo returning from the far boundary of said tissue segment and from the amplitude modulation function of the pulse which caused a white echo to be generated from said near boundary, the amplitude modulation of a pulse which when transmitted, would cause a white echo to be generated from said far boundary;
h. determining the attenuation coefficient of said tissue segment as a function of the amplitude modulation function of the pulse which generates a white echo from said near boundary, the amplitude modulation function determined in step (g) and the thickness of said tissue segment.

13. The method claimed in claim 12 wherein said transmitted pulses have the general form $$S(t) = g|H^{-1}(f)|\sqrt{W(f)}e^{\gamma f}\sin 2\pi \int f dt$$

where
g is the system gain control,
$|H^{-1}(f)|$ is the transmitter-transducer-receiver spectrum amplitude correction function,
$\sqrt{W(f)}$ is a weighting function for improving axial resolution,
f is the instantaneous frequency of the frequency modulating function and is equal to $f_o + \Delta f(t)$,
$f_o$ is the initial frequency value of the frequency modulating function, and
Δf(t) is a general function of time.

14. The method claimed in claim 13 wherein:

$$\Delta f(t) = \Delta f'(O)t + \Delta f''(O)\frac{t^2}{2}$$

where Δf'(0) is the first derivative of Δf(t) with respect to time at t=0 and Δf''(0) is the second derivative of Δf(t) with respect to time at t=0.

15. The method claimed in claim 14 wherein $$\Delta f(t) = Bt,$$

where B is the rate of change in frequency of f; and wherein
W(f) is the Hamming function, and $$W(f) = 0.54 - 0.46 \cos(2\pi f/\Delta f).$$

16. The method claimed in claim 14 wherein:
step (b) is effected by adjusting the value of $\Delta f(t)$ of the transmitted pulse; and,
step (d) is effected by adjusting the value of $\gamma$ of the transmitted pulse.

17. The method claimed in claim 16 wherein step (g) comprises the steps of:
converting said echo to an electrical signal;
introducing said electrical signal into the inputs of a pair of matched filters;
computing the normalized difference, $d(\tau)$, of the outputs of said filters; and,
computing the constant $\gamma$ as a function of the value of $\gamma$ of said transmitted pulse, said normalized difference and the frequency range of said echo.

18. The method claimed in claim 17 wherein said constant $\gamma$ is computed from the expression:

$$\gamma = \gamma' + d(\tau)/(0.08\Delta f)$$

where $\gamma'$ is the value of $\gamma$ of said transmitted pulse.

19. The method claimed in claim 18 wherein said attenuation coefficient is computed using the following formula:

$$a_j = (\gamma_j - \gamma_i)/2X_j$$

where
$a_j$ is the attenuation coefficient of the tissue segment,
$\gamma_i$ is the value of $\gamma$ of a transmitted pulse necessary to generate a white echo from said near boundary,
$\gamma_j$ is the value of $\gamma$ of a transmitted pulse necessary to generate a white echo from said far boundary; and,
$X_j$ is the thickness of said tissue segment.

20. A method of detecting abnormalities in a series of adjacent tissue segments comprising the steps of:
a. transmitting an amplitude and frequency modulated ultrasonic pulse into said tissue segments;
b. adjusting said frequency modulation of said pulse and transmitting said pulse into said tissue segments if said tissue segments are dispersive and if the echo returning from the near boundary of the first tissue segment to be analyzed is not frequency modulated linearly;
c. repeating steps (a) and (b) until an echo is received from said near boundary which is frequency modulated linearly if said tissue segments are dispersive;
d. adjusting the amplitude modulation of said pulse and transmitting said adjusted pulse into said tissue segments if said echo received in step (c) is not white;
e. repeating step (d) until said echo returning from said near boundary is white;
f. transmitting an ultrasonic into said pulse tissue segments, said pulse having substantially the same waveshape as the pulse which caused a white echo to be generated from said near boundary;
g. determining from the spectrum amplitude of the echo returning from the far boundary of said first tissue segment and from the amplitude modulation function of the pulse which caused said white echo to be generated from said near boundary, the amplitude modulation of a pulse which, when transmitted, would cause a white echo to be generated from said far boundary;
h. determining the attenuation coefficient of said tissue segment as a function of the amplitude modulation function of the pulse which generated a white echo from said near boundary, the amplitude modulation function determined in step (g) and the thickness of said first tissue segment;
i. transmitting an ultrasonic pulse into said tissue segments;
j. determining from the spectrum amplitude of the echo returning from the far boundary of the next farthest adjacent tissue segment and from the amplitude modulation function of the pulse which was determined would cause a white echo to be generated from the far boundary of the next nearest adjacent tissue segment, the amplitude modulation function of a pulse which, when transmitted, would cause a white echo to be generated from the far boundary of said next farthest adjacent tissue segment;
k. determining the attenuation coefficient of said next farthest tissue segment as a function of the amplitude modulation function of the pulse which was determined would generate a white echo from the far boundary of the next nearest adjacent tissue segment, the amplitude modulation function determined in step (j) and the thickness of said next farthest tissue segment;
l. repeating steps (i) through (k) for each tissue segment to be analyzed.

21. The method claimed in claim 20 wherein said transmitted pulses have the general form $$S(t) = g|H^{-1}(f)|\sqrt{W(f)}e^{\gamma f} \sin 2\pi \int f dt$$

where
g is the system gain control,
$|H^{-1}(f)|$ is the transmitter-transducer-receiver spectrum amplitude correction function,
$\sqrt{W(f)}$ is a weighting function for improving axial resolution,
f is the instantaneous frequency of the frequency function and is equal to $f_o + \Delta f(t)$,
$f_o$ is the initial frequency value of the frequency modulating function, and
$\Delta f(t)$ is a general function of time.

22. The method claimed in claim 21 wherein:

$$\Delta f(t) = \Delta f'(O)t + \Delta f''(O)\frac{t^2}{2}$$

where $\Delta f'(0)$ is the first derivative of $\Delta f(t)$ with respect to the time at $t=0$ and $\Delta f''(0)$ is the second derivative of $\Delta f(t)$ at $t=0$.

23. The method claimed in claim 21 wherein $$\Delta f(t) = Bt,$$

where B is the rate of change in frequency of f; and wherein

W(f) is the Hamming function, and $$W(f) = 0.54 - 0.46 \cos(2\pi f/\Delta f)$$

24. The method claimed in claim 22 wherein:
step (b) is effected by adjusting the value of $\Delta f(t)$ of the transmitted pulse; and,
step (d) is effected by adjusting the value of $\gamma$ of the transmitted pulse.

25. The method claimed in claim 24 wherein step (g) comprises the steps of:
converting said echo to an electrical signal;
introducing said electrical signal into the inputs of a pair of matched filters;
computing the normalized difference, $d(\tau)$, of the outputs of said filters; and,
computing the constant $\gamma$ as a function of the value of said transmitted pulse, said normalized difference and the frequency range of said echo.

26. The method claimed in claim 24 wherein said constant $\gamma$ is computed from the expression:

$$\gamma = \gamma' + d(\tau)/(0.08\Delta f)$$

where $\gamma'$ is the value of $\gamma$ of said transmitted pulse.

27. The method claimed in claim 26 wherein said attenuation coefficient is computed using the following formula:

$$\alpha_j = (\gamma_j - \gamma_i)/2X_j$$

where
$\alpha_j$ is the attenuation coefficient of the tissue segment,
$\gamma_i$ is the value of $\gamma$ of a transmitted pulse necessary to generate a white echo from said near boundary,
$\gamma_j$ is the value of $\gamma$ of a transmitted pulse necessary to generate a white echo from said far boundary; and,
$X_j$ is the thickness of said tissue segment.

28. A method for detecting a pair of boundaries within a body of material and determining the attenuation coefficient of the material between said boundaries comprising the steps of:
a. transmitting into said material a first sonic pulse such that the echo returning from a first boundary within said material is white;
b. transmitting into said material a second sonic pulse such that the echo returning from a second adjacent boundary within said material is white;
c. determining the attenuation coefficient of the material between said boundaries as a function of said transmitted pulses and the thickness of material between said boundary.

29. The method claimed in claim 28 wherein the steps of transmitting said sonic pulses comprise:
transmitting into said material a first series of sonic pulses until a white echo is detected the shape of each pulse in said series being different from the shape of the immediate previous pulse in said first series of pulses.

30. The method claimed in claim 28 wherein the steps of transmitting said sonic pulses comprise:
transmitting a sonic pulse into said material;
determining whether the echo returning from the appropriate boundary of said material is white;
modifying the shape of said pulse;
repeating the three previous steps until said returning echo is white.

31. The method claimed in claim 28 wherein the step of transmitting a sonic pulse comprises:
creating an electrical signal having a form $$S(t) = g|H^{-1}(f)|\sqrt{W(f)}e^{\gamma f} \sin 2\pi \int f dt$$

where
g is the system gain control,
$|H^{-1}(f)|$ is the transmitter-transducer-receiver spectrum amplitude correction function,
$\sqrt{W(f)}$ is a weighting function for improving axial resolution,
f is the instantaneous frequency of the frequency function and is equal to $f_o + \Delta f(t)$,
$f_o$ is the initial frequency value of the frequency modulating function, and
$\Delta f(t)$ is a general function of time
converting said electrical signal into said sonic pulse of the same form; and,
directing said sonic pulse into said material.

32. The method claimed in claim 31 wherein:

$$\Delta f(t) = \Delta f'(0)t + \Delta f''(0)\frac{t^2}{2}$$

where $\Delta f'(0)$ is the first derivative of $\Delta f(t)$ with respect to the time at $t=0$ and $\Delta f''(0)$ is the second derivative with respect to time of $\Delta f(t)$ at $t=0$.

33. The method claimed in claim 30 wherein the steps of determining whether said echoes are white comprise:
converting into an electrical signal the echo returning from the appropriate boundary of said material;
introducing said electrical signal into a pair of matched filters;
computing the normalized difference of the outputs of said matched filters; and,
comparing said normalized difference to zero, said normalized difference being substantially zero when the input to said matched filters is white.

34. The method claimed in claim 33 wherein said normalized differences are computed by using the following equation:

$$d(\tau) = [r_L(\tau) - r_H(\tau)]/[r_L(\tau) + r_H(\tau)]$$

where $d(\tau)$ is the normalized difference of the outputs of the matched filters, $r_H(\tau)$ is the peak output of said high frequency filter and $r_L(\tau)$ is the peak output of said low frequency filter.

35. The method claimed in claim 28 further comprising the steps of:
transmitting into said material prior to transmitting each of said series of pulses, an initial series of sonic pulses until the echo returning from the boundary under analysis is frequency modulated linearly.

36. The method claimed in claim 34 wherein the attenuation coefficient of said material between said boundaries is computed using the following equation:

$$\alpha_j = (\gamma_j - \gamma_i)/2X_j$$

where $\alpha_j$ is the attenuation coefficient of the material between said boundaries, $\gamma_i$ and $\gamma_j$ are the values of $\gamma$ in the expression describing the pulses of said series of pulses which causes a white echo to return from the near boundary of said material and which causes a white echo to return from the far boundary of said material, and $X_j$ is the thickness of said material between said boundary.

37. An apparatus for detecting abnormalities in a series of adjacent tissue segments comprising:
- transmitting means for transmitting ultrasonic pulses into said tissue segments;
- receiving means for receiving ultrasonic echoes returning from the boundaries of said tissue segments;
- analyzing means connected to said receiving means for determining whether said returning echoes are white;
- adjusting means for adjusting the shape of said transmitted pulses;
- computing means connected to said receiving means for computing the attenuation coefficients of said tissue segments;
- display means connected to said computing means for displaying said attenuation coefficients; and,
- controlling means for controlling the sequence of operation of said transmitting, receiving, analyzing, computing, and display means.

38. The apparatus as claimed in claim 37 wherein said transmitting means comprises:
- generating means for generating an electrical signal of the form:

$$S(t) = g|H^{-1}(f)| \sqrt{W(f)} \, e^{\gamma f} \sin 2\pi (f_o + \frac{\Delta f(O)t}{2} + \Delta f'(O)\frac{t^2}{6}) t$$

where
- g is the system gain control,
- $|H^{-1}(f)|$ is the transmitter-transducer-receiver spectrum amplitude correction function,
- $\sqrt{W(f)}$ is a weighting function for improving axial resolution,
- f is the instantaneous frequency of the frequency modulating function and is equal to $f_o + \Delta f(t)$,
- $f_o$ is the initial frequency value of the frequency modulating function,
- $\Delta f(t)$ is a general function of time,
- $\Delta f'(0)$ is the first derivative of $\Delta f(t)$ with respect to time at t=0, and,
- $\Delta f''(0)$ is the second derivative of $\Delta f(t)$ with respect to time at t=0, and,

- a transducer for converting said electrical signal into an ultrasonic pressure pulse.

39. The apparatus claimed in claim 37 wherein said receiving means comprises:
- a transducer for converting ultrasonic echoes returning from said tissue segments to electrical signals;
- amplifying means for amplifying said signals;
- an intermediate frequency oscillator;
- mixing means for electrically mixing the outputs of said amplifier and said oscillator;
- a pair of matched filters connected in parallel to the output of said mixer, the center frequency of said matched filters being equal to the operating frequency of said oscillator; and,
- a pair of envelope followers one connected to the output of each matched filter.

40. The apparatus claimed in claim 39 wherein said matched filters comprise:
- a high frequency filter having a Fourier spectrum amplitude impulse response $H_H(f)$; and
- a low frequency filter having a Fourier spectrum amplitude impulse response $H_L(f)$.

41. The apparatus as claimed in claim 40 wherein said analyzing means comprises:
- peak recording means for detecting and saving the peak amplitude of the output of said matched filters;
- switching means connected to the output of said envelope followers and said peak recording means;
- timing means for determining when an echo to be analyzed has returned to said transducer, connected to said switching means; and,
- computing means for computing the normalized difference of the outputs of said matched filters connected to the outputs of said peak recording means.

42. The apparatus claimed in claim 41 wherein said controlling means is a microprocessor.

43. The apparatus claimed in claim 42 wherein said switching means is a field effect transistor.

44. The apparatus claimed in claim 43 wherein said timing means is a programmable down-counter.

* * * * *

UNITED STATES PATENT AND TRADEMARK OFFICE
CERTIFICATE OF CORRECTION

PATENT NO. : 4,202,215
DATED : May 13, 1980
INVENTOR(S) : Charles R. Meyer

It is certified that error appears in the above-identified patent and that said Letters Patent are hereby corrected as shown below:

Column 2, line 22, delete "are" and substitute --is--

Column 2, line 62, underscore "In Vitro"

Column 5, line 25, insert --,-- after "Iterative"

Column 5, line 26, underscore "In Vivo"

Column 8, line 6, Equation 13, delete "$\Delta f(0)t$" and substitute --$\Delta f'(0)t$--

Column 8, line 6, Equation 13, delete "$\Delta f'(0)$" and substitute --$\Delta f''(0)$--

Column 8, line 9, delete "$\Delta f(0)$" and substitute --$\Delta f'(0)$--

Column 8, line 9, delete "$\Delta f'(0)$" and substitute --$\Delta f''(0)$--

Column 8, line 51, delete "$\int \alpha(f,l)dl$" and substitute --$\int \alpha(f'l)$--

Column 10, line 62, Equation 18, delete "$\Delta f(0)t$" and substitute --$\Delta f'(0)t$--

Column 10, line 62, Equation 18, delete "$\Delta f'(0)t^2$" and substitute --$\Delta f''(0)t^2$--

Column 13, line 25, delete "$\Delta f(0)t$" and substitute --$\Delta f'(0)t$--

Column 13, line 25, delete "$\Delta f'(0)$" and substitute --$\Delta f''(0)$--

Column 17, line 8, delete "$\Delta f(0)t$" and substitute --$\Delta f'(0)t$--

Column 17, line 8, delete "$\Delta f'(0)$" and substitute --$\Delta f''(0)$--

UNITED STATES PATENT AND TRADEMARK OFFICE
CERTIFICATE OF CORRECTION

PATENT NO. : 4,202,215
DATED : May 13, 1980
INVENTOR(S) : Charles R. Meyer

It is certified that error appears in the above-identified patent and that said Letters Patent are hereby corrected as shown below:

Column 18, line 63, delete "$\Delta f(0)t$" and substitute --$\Delta f'(0)t$--

Column 18, line 63, delete "$\Delta f'(0)$" and substitute --$\Delta f''(0)$--

Column 20, line 58, delete "$\Delta f(0)t$" and substitute --$\Delta f'(0)t$--

Column 20, line 58, delete "$\Delta f'(0)$" and substitute --$\Delta f''(0)$--

Column 21, line 19, delete "24" and substitute --25--

Column 22, line 23, delete "$\Delta f(0)t$" and substitute --$\Delta f'(0)t$--

Column 22, line 23, delete "$\Delta f'(0)$" and substitute --$\Delta f''(0)$--

Column 23, line 27, delete "$\underline{\Delta f(0)t}\atop 2$" and substitute --$\underline{\Delta f'(0)t}\atop 2$--

Column 23, line 27, delete "$\Delta f'(0)\frac{t^2}{6})t$" and substitute --$\Delta f''(0)\frac{t^2}{6})t$--

Signed and Sealed this

*Fourteenth* Day of *October 1980*

[SEAL]

*Attest:*

SIDNEY A. DIAMOND

*Attesting Officer*     *Commissioner of Patents and Trademar*